United States Patent [19]
Davis et al.

[11] Patent Number: 6,043,064
[45] Date of Patent: Mar. 28, 2000

[54] ENZYMATIC HYDROXYLATION PROCESS FOR THE PREPARATION OF HMG-COA REDUCTASE INHIBITORS AND INTERMEDIATES THEREOF

[75] Inventors: Brian L. Davis, Milltown; Paul M. Cino, Bound Brook; Laszlo Szarka, East Brunswick, all of N.J.

[73] Assignee: Bristol-Myers Squibb Company, Princeton, N.J.

[21] Appl. No.: 08/141,316

[22] Filed: Oct. 22, 1993

[51] Int. Cl.[7] .................................. C12P 7/02; C12P 7/00
[52] U.S. Cl. ..................... 435/155; 435/132; 435/125; 435/252.1; 435/253.2; 435/253.4; 435/146; 435/872; 435/886
[58] Field of Search ...................... 435/155, 132, 435/125, 252.1, 253.2, 253.4, 872, 886, 146

[56] References Cited

U.S. PATENT DOCUMENTS

| | | | |
|---|---|---|---|
| 3,983,140 | 9/1976 | Endo et al. | 424/279 |
| 4,206,206 | 6/1980 | Mori et al. | 424/181 |
| 4,346,227 | 8/1982 | Terahara et al. | 560/119 |
| 4,444,784 | 4/1984 | Hoffman et al. | 560/119 |
| 4,448,979 | 5/1984 | Terahara et al. | 424/279 |
| 4,450,171 | 5/1984 | Hoffman et al. | 560/119 |
| 4,537,859 | 8/1985 | Terahara et al. | 624/279 |

FOREIGN PATENT DOCUMENTS

| | | |
|---|---|---|
| 251625 | 1/1988 | European Pat. Off. . |
| 408806 | 1/1991 | European Pat. Off. . |
| 465265 | 1/1992 | European Pat. Off. . |
| 486153 | 5/1992 | European Pat. Off. . |
| 60-176595 | 2/1985 | Japan . |
| 2111052 | 6/1983 | United Kingdom . |

OTHER PUBLICATIONS

*ATCC Catalogue of Bacteria & Phages.* 7th. 1989. pp. 16 & 190.

*Primary Examiner*—Leon B. Lankford, Jr.
*Attorney, Agent, or Firm*—Burton Rodney

[57] ABSTRACT

An enzymatic hydroxylation process for the preparation of compounds useful as HMG-CoA reductase inhibitors and/or as intermediates in the preparation of HMG-CoA reductase inhibitors uses a microorganism or an enzyme derived from, or having the structure of an enzyme derived from, said microorganism, which is capable of catalyzing the hydroxylation process.

18 Claims, No Drawings

ENZYMATIC HYDROXYLATION PROCESS FOR THE PREPARATION OF HMG-COA REDUCTASE INHIBITORS AND INTERMEDIATES THEREOF

FIELD OF THE INVENTION

The present invention relates to an enzymatic hydroxylation process for the preparation of compounds useful as HMG-CoA reductase inhibitors and/or as intermediates in the preparation of HMG-CoA reductase inhibitors.

SUMMARY OF THE INVENTION

The present invention provides a method for the preparation of a compound of the formula I:

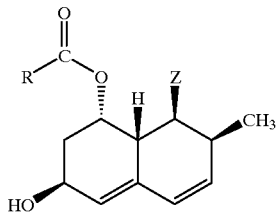

(I)

its partially or completely hydrogenated analogs or a salt thereof, wherein

R is alkyl or aryl;

Z is the open chain moiety

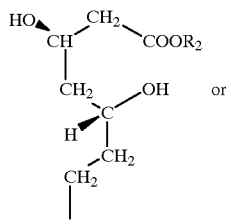

or the lactone

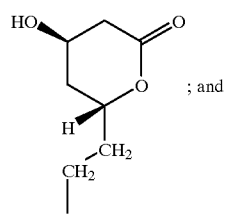

; and $R^2$ is hydrogen, alkyl, ammonium, alkyl-ammonium or alkali metal;

comprising the step of contacting a compound of the formula II:

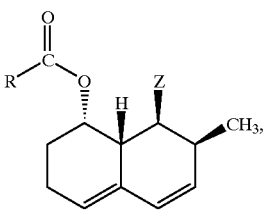

(II)

a partially or completely hydrogenated analog or a salt thereof, wherein R, Z and $R^2$ are as defined for formula I, with a microorganism, or with an enzyme derived from, or having the structure of an derived from said microorganism, which is capable of catalyzing the hydroxylation of said compound of the formula II to yield said compound of the formula I, and effecting said hydroxylation;

where said microorganism is selected from the genera Nocardia, Amycolata, Saccharopolyspora, Streptomyces, Amycolatopsis, Saccharothrix or Gilbertella, provided that when the compound of formula II is compactin, the microorganism is not Amycolata, Nocardia or Streptomyces.

The enzymatic hydroxylation process of the present invention provides an efficient means for obtaining compounds of the formula I, which may themselves exhibit HMG-CoA reductase inhibitory activity, and/or which may be used as intermediates in the preparation of other HMG-CoA reductase inhibitors. Reduction or elimination of byproducts may be achieved by employing the hydroxylation method of the present invention, which method may also be conducted under mild reaction conditions.

DETAILED DESCRIPTION OF THE INVENTION

The method of the present invention is described further as follows.

Definitions

The terms "enzymatic process" or "enzymatic method" as used herein denote a process or method employing an enzyme or microorganism.

The term "alkyl" as used herein, alone or as part of another group, denotes both straight and branched chain, optionally substituted hydrocarbons containing 1 to 12 carbons in the normal chain, preferably 1 to 6 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like. Exemplary substituents may include one or more groups selected from the following: halo (especially chloro), trihalomethyl, alkoxy (for example, where two alkoxy substituents form an acetal), aryl such as unsubstituted aryl (e.g., phenyl), alkyl-aryl or haloaryl, cycloalkyl such as unsubstituted cycloalkyl or alkyl-cycloalkyl, hydroxy or protected hydroxy, carboxyl, alkyloxy-carbonyl, alkylamino, dialkylamino such as dimethylamino, alkylcarbonylamino such as acetylamino, amino, arylcarbonylamino, nitro, cyano, thiol, or alkylthio. Preferred alkyl substituents are hydroxy groups.

The term "alkenyl" as employed herein, alone or as part of another group, denotes optionally substituted straight or branched chain hydrocarbon groups as described above for alkyl, further containing at least one carbon to carbon double bond.

The term "cycloalkyl" as employed herein, alone or as part of another group, denotes an optionally substituted, saturated homocyclic carbon ring system, preferably containing from 1 to 3 rings and from 3 to 12, preferably from 3 to 8, carbons per homocyclic ring, such as cyclopropyl, cyclobutyl, cyclopentyl, cyclohexyl, cycloheptyl, cyclooctyl, cyclodecyl, cyclododecyl, and adamantyl. Exemplary optional substituents include one or more alkyl groups as described above, or one or more of those groups described above as alkyl substituents.

The term "aryl" as used herein denotes monocyclic or bicyclic substituted or unsubstituted aromatic groups containing from 6 to 12 carbons in the ring portion, such as phenyl, biphenyl, naphthyl, substituted phenyl, substituted biphenyl or substituted naphthyl. Exemplary substituents (preferably three or fewer) include one or more of the following groups: alkyl such as unsubstituted alkyl, haloalkyl or cycloalkylalkyl, halogen, alkoxy such as unsubstituted alkoxy or haloalkoxy, hydroxy, aryl such as phenyl or halophenyl, aryloxy such as phenoxy, alkylcarbonyloxy or aroyloxy, allyl, cycloalkyl, alkylamino, dialkylamino, amido such as alkylcarbonylamino or arylcarbonylamino, amino, nitro, cyano, alkenyl, thiol, alkylcarbonyl, or arylcarbonyl, or methylenedioxy where the methylene group may be substituted by lower alkyl group(s) (that is, alkyl groups as described above having 1 to 6 carbon atoms), arylalkenyl group(s), and/or alkylthio group(s).

The terms "halo" or "halogen" as used herein denote chlorine, fluorine, bromine or iodine.

The term "salt(s)" as employed herein refers to acidic and/or basic salts formed with inorganic and/or organic bases. The nontoxic, pharmaceutically acceptable salts are preferred. Exemplary pharmaceutically acceptable salts include those formed from cations such as sodium, potassium, aluminum, calcium, lithium, magnesium, zinc and tetramethylammonium as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2pyrrolidine-1'-yl-methylbenzimidazole, diethylamine, piperazine and tris(hydroxymethyl) aminomethane.

The term "pharmaceutically acceptable cation" denotes a positive counterion forming a pharmaceutically acceptable salt, such as those described above.

The term "ATCC" as used herein refers to the accession number of the American Type Culture Collection, 12301 Parklawn Drive, Rockville, Md. 20852, an organism depository.

Starting Materials

Compounds of the formula II to be employed in the hydroxylation method of the present invention may be obtained by methods known to the skilled artisan. Such compounds are disclosed, for example, in U.S. Pat. No. 4,450,171.

Preferred Compounds

Compounds of the formula I having the following formula Ia are preferred:

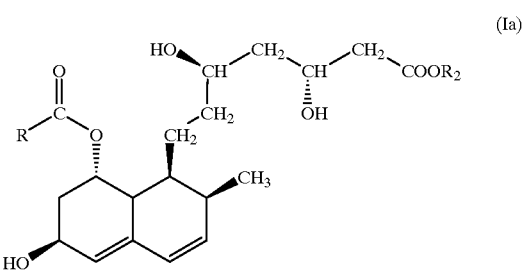

(Ia)

its partially or completely hydrogenated analogs or alkali metal salts thereof, wherein R is alkyl and $R^2$ is as defined in formula I.

A particularly preferred example is:

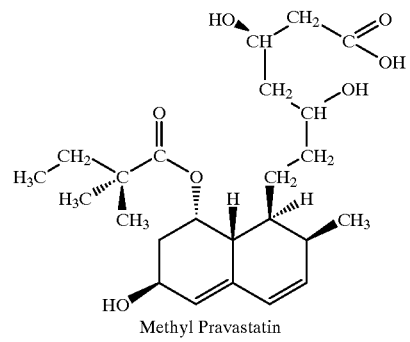

Methyl Pravastatin its partially or completely hydrogenated analogs or alkali metal salts thereof.

Compounds of the formula II having the following formula IIa are preferred for use as the starting material:

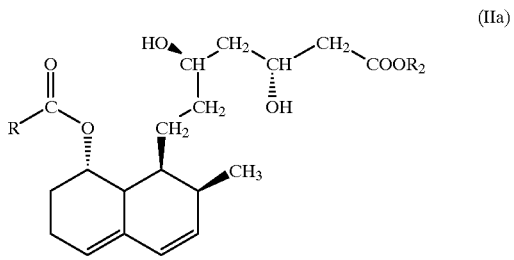

(IIa)

its partially or completely hydrogenated analogs or alkali metal salts thereof, wherein R is alkyl and $R^2$ is as defined in formula II. A particularly preferred example is

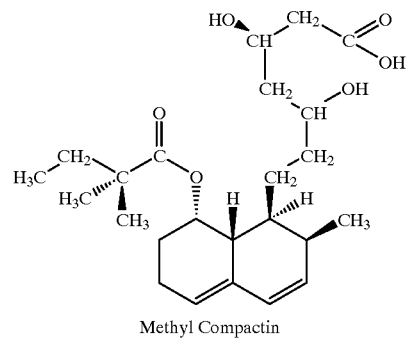

Methyl Compactin its partially or completely hydrogenated analogs or alkali metal salts thereof.

Compounds of the formula I, or any compound described herein, in which one or more of the double bonds is absent, may be obtained by hydrogenating the corresponding compound in which such bonds are present according to methods known to the skilled artisan.

Any of the products of the present method may be isolated and purified by known methodologies such as by filtering off cells or cellular materials where appropriate, extraction, crystallization, thin layer or column chromatography, high performance liquid chromatography and the like.

The above structures shown for methyl compactin and methyl pravastatin are referred to herein as the acid form of these compounds. Where the carboxyl group of these compounds is in the alkali metal salt form, the compounds are referred to herein as the salt form.

As discussed below, the use of an aqueous medium is preferred in conducting the hydroxylation method of the present invention. It is therefore preferred to prepare, or to employ as starting materials, those compounds in which Z is the open chain moiety as defined above since such compounds are relatively more water soluble than the corresponding compounds in which Z is a lactone moiety. Compounds of the formula II in which Z is a lactone moiety may, for example, be hydrolyzed to the open chain form prior to use in the process of the present invention.

Enzymes and Microorganisms

The enzyme or microorganism employed in the method of the present invention may be any enzyme or microorganism, regardless of origin or purity, having the ability to catalyze the conversion as described herein. Genera of microorganisms suitable as sources of catalyzing enzymes include Nocardia, Amycolata, Saccharopolyspora, Streptomyces, Amycolatopsis, Saccharothrix or Gilbertella.

Exemplary species suitable for use in the present invention include *Amycolata autotrophica* such as ATCC 35204, *Streptomyces californicus* such as ATCC 15436, *Amycolatopsis mediterranei* such as ATCC 21411, *Saccharothrix australensis* such as ATCC 31497, *Gilbertella persicaria* such as ATCC 38591, *Saccharopolyspora hirsuta* such as ATCC 27875, 27876 or 20501, *Saccharopolyspora erythraea* such as ATCC 11635, and the like. Particularly preferred are *Amycolata autotrophica* such as ATCC 35204 and *Saccharopolyspora hirsuta* such as ATCC 20501.

With respect to the use of microorganisms, the method of the present invention may be carried out using any microbial cellular material having the ability to catalyze the conversion as described herein. The cells may be used in the form of intact wet cells or dried cells such as lyophilized, spray-dried or heat-dried cells. Cells may also be used in the form of treated cell material such as ruptured cells or cell extracts. The cells or cellular materials, such as isolated fungal mycelia, may be employed in the free state or immobilized on a support such as by physical adsorption or entrapment. One or more species of microorganism may be employed when carrying out the instant process.

The method of the present invention may be carried out subsequent to the growth of the microorganism(s) employed, for example, by growing the microorganism(s) either in the presence or absence of a compound of the formula II starting material, harvesting and, preferably, washing (e.g., with water) the microbial materials, and then contacting the microbial materials obtained with the compound of the formula II starting material. The method of the present invention may also be carried out by in situ fermentation and reaction, that is, reaction in the presence of actively growing microorganisms.

The reaction may be conducted under quiescent (static) conditions, or by employing agitation. Agitation, such as shake-flask culture or aeration and agitation, is preferably employed when the compound of the formula II starting material is added to actively growing cultures. In such cases, an anti-foaming agent may be employed.

The growth of microorganisms may be achieved by the skilled artisan, for example, by the use of an appropriate medium containing nutrients such as carbon and nitrogen sources and trace elements. Exemplary assimilable carbon sources include glucose, glycerol, maltose, dextrin, starch, lactose, sucrose, molasses, soybean oil, cotton seed oil, etc. Exemplary assimilable nitrogen sources include soybean meal, peanut meal, cotton seed meal, fish meal, corn steep liquor, peptone, rice bran, meat extract, yeast, yeast extract, sodium nitrate, ammonium nitrate, ammonium sulfate, etc. Inorganic salts such as sodium chloride, phosphates, calcium carbonate, etc., may be added to the culture medium. A minor amount of a metal salt or heavy metal may also be added.

The same or different media may be employed at various stages of the growth of the microorganisms. Preferred media for the growth of microorganisms are those described in the examples herein, which media may be employed for the growth of any microorganism employed in the method of the present invention.

Enzymes, when employed, are preferably derived from the aforementioned microorganisms, or they may be synthetically or otherwise prepared. For example, they may be derived from genetically engineered host cells. The use of the genetically engineered host cells themselves, or cells which have otherwise been modified, is also contemplated where such cells are capable of producing enzymes having the structure of enzymes derived from the above recited genera of microorganisms.

Reaction Conditions

The method of the present invention may be conducted in an aqueous medium, such as a buffered aqueous medium. The aqueous phase is conveniently water, preferably deionized water, or a suitable aqueous buffer solution, especially a phosphate buffer solution. Use of an aqueous medium is preferred for the present hydroxylation method.

The reaction in the present invention may also be conducted in an organic medium or in a medium which is a mixture of an organic medium and an aqueous medium. Use of an organic or organic/aqueous medium may enhance solubilization of the less water soluble compounds of the formula II starting materials, such as those where Z is a lactone moiety. Less water soluble starting materials may, for example, be dissolved in an organic solvent such as methyl or ethyl alcohol, and the solution added to an aqueous medium for conversion. Liquids forming such organic media may be immiscible in water or, preferably, may be miscible in water. Exemplary organic media include toluene, hexane, benzene, acetone, dimethylsulfoxide, cyclohexane, xylene, trichlorotrifluoroethane, alkanols such as methyl or ethyl alcohol or butanol, and the like.

It is preferred that the starting material is dissolved, for example, in water or an alcohol, prior to addition to the reaction medium.

The reaction medium preferably contains between about 0.5 to about 3 mg of a compound of the formula II starting compound per ml of liquid medium. The pH of the reaction medium is preferably between about 6.0 and about 7.5.

To carry out the hydroxylation reaction of the present invention, water or an organic alcohol, for example, an alkanol such as methyl or ethyl alcohol, may be added. It is preferred to employ these materials in an amount providing a molar excess, preferably a large molar excess, based on the compound of formula II starting material.

The amount of microbial cells added, where employed in the present process, is preferably an amount ranging from about 10 to about 1000 mg per mg of the compound of formula II starting material. The amount of enzyme added, where employed in the present process, is preferably an amount ranging from about 1 to about 100 mg per mg of the compound of formula II starting material.

The reaction medium is preferably held at a temperature between about 27 and 40° C., and is most preferably held between about 28 and about 34° C. The reaction time can be appropriately varied depending upon the amount of enzyme produced by the microbial cells, or used per se, and its specific activity. Typical reaction times are between about 2.5 hours and about 72 hours. Reaction times may be reduced by increasing the reaction temperature and/or increasing the amount of enzyme added to the reaction solution.

Preparation of HMG-CoA Reductase Inhibitors

HMG-CoA reductase (3-hydroxy-3-methylglutaryl coenzyme A reductase, EC 1.1.1.34) is a key enzyme in cholesterol biosynthesis. Inhibitors of this enzyme find utility as anticholesterolemic agents, that is, in lowering or maintaining plasma cholesterol levels. In addition to the treatment and prevention of hypercholesterolemia, HMG-CoA reductase inhibitors find utility in the treatment and prevention of atherosclerosis, hyperlipoproteinaemia, and/or hyperlipidemia.

Compounds of the formula II described above may themselves exhibit HMG-CoA reductase inhibiting activity (e.g., methyl compactin), and/or may be employed as intermediates in the preparation of other compounds having HMG-CoA reductase inhibiting activity. In the latter case, the present invention further provides a method wherein hydroxylation is conducted according to the above-described method of the present invention and, subsequently, the hydroxylated product so formed is employed in the preparation of an HMG-CoA reductase inhibitor (e.g., groups are deprotected, added or otherwise modified thereon). Preferably, the inhibitor so prepared has enhanced HMG-CoA reductase inhibiting activity relative to any such activity the hydroxylated product from which it is prepared may possess.

HMG-CoA reductase inhibitors obtained according to the method of the present invention may, for example, be administered to mammals, particularly humans, by modes and in dosages selected according to methods known to the skilled artisan.

A particularly preferred method for the preparation of an HMG-CoA reductase inhibitor of the present invention is that comprising the steps of:

(A) hydroxylating a compound of the formula IIa, wherein R is

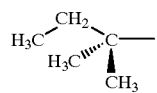

and $R^2$ is H, or a salt thereof with Amycolata autotrophica (ATCC 35204) or Saccharopolyspora hirsuta subspecies kobensis (ATCC 20501) to yield methyl pravastatin having the structure:

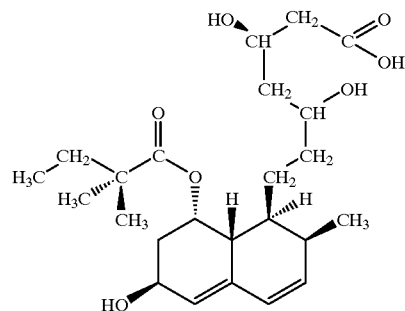

or the alkali metal, especially sodium or lithium, salt thereof.

The following Examples illustrate preferred embodiments of the present invention, and are not intended to limit the scope or spirit of the instant claims. The components of the media employed in these Examples are as follows.

| Medium | Media Compositions |
| --- | --- |
| F7 | malt extract 10 g/L, yeast extract 10 g/L, peptone 1 g/L, dextrose 20 g/L, distilled water to one liter, pH adjusted to 7.0 before sterilization by autoclaving |
| K28 | Pharmamedia 25 g/L, cerelose 69 g/L, $CaCO_3$ 9 g/L, $K_2HPO_4$ 0.1 g/L, tap water to one liter, pH adjusted to 6.8–7.0 before sterilization by autoclaving |
| F4 | tryptone 5 g/L, malt extract 3 g/L, glucose 10 g/L, yeast extract 3 g/L, distilled water to one liter, sterilize in autoclave |
| F46 | glycerol 10 g/L, maltose 40 g/L, toasted Nutrisoy flour 30 g/L, peptone 10 g/L, spray dried corn steep liquor 10 g/L, $MgSO_4 \cdot 7H_2O$ 0.5 g/L, tap water to one liter, pH adjusted to 5.3 before sterilization by autoclaving |
| M124 | cerelose 10 g/L, NZ Amine B 15 g/L, yeast extract 10 g/L, NaCl 5 g/L, $CaCO_3$ 1 g/L, tap water to one liter, pH adjusted to 6.8–7.0 before sterilization by autoclaving |
| Mueller-Hinton Broth (Difco brand) | beef infusion 300 g/L, casamino acids, technical 17.5 g/L, starch 1.5 g/L, suspended in one liter distilled or deionized water and heated to boiling to dissolve completely, final pH 7.4 |
| Trypticase Soy Broth, BBL brand | trypticase peptone 17 g/L, phytone peptone 3 g/L, NaCl 5 g/L, $K_2HPO_4$ 2.5 g/L, dextrose 2.5 g/L, distilled water to one liter, sterilize in autoclave |
| Y17 | yeast nitrogen base 6.7 g/L, glucose 50 g/L, Sigma adenine HCl 0.09 g/L, Sigma l-tyrosine 0.06 g/L, heat to |

-continued

| Medium | Media Compositions |
|--------|-------------------|
|        | boil and mix Difco casamino acids 2 g/L, agar 20 g/L, distilled water to one liter, sterilize in autoclave |

EXAMPLE 1

One frozen vial of *Amycolata autotrophica* (ATCC 35204) and one frozen vial of *Saccharopolyspora hirsuta* subspecies *kobensis* (ATCC 20501) were thawed and used to inoculate separate 500 ml flasks containing 100 ml each of medium F4. Each flask was placed on a shaker at approximately 280 rpm, at 25° C., and shaken for 72 hours. Aliquots of 2.5 ml apiece of the 72 hour A. autotrophica culture broth were used to inoculate six 250 ml flasks containing 50 ml of medium F7 and six 250 ml flasks containing 50 ml of medium K28. Similarly, aliquots of 2.5 ml apiece of the 72 hour *S. hirsuta* culture broth were used to inoculate six 250 ml flasks containing 50 ml of medium F7 and six 250 ml flasks containing 50 ml of medium K28. Accordingly, there were 24 flasks in total. All 24 flasks were placed on a shaker and shaken at approximately 280 rpm at 25° C.

After 24 hours of shaking, 1 ml of filter-sterilized 5 mg/ml methyl compactin salt solution was added aseptically to three F7 flasks and three K28 flasks of each culture. (Salt solution was prepared from the lactone by dissolving the lactone in a minimal volume of ethanol, adding about 15 ml of water [which produces some precipitate], adjusting the pH to about 11.8, incubating in a 65° C. waterbath until the precipitate dissolved, and carefully bringing the pH down to 7.5. Distilled water was added to bring the calculated concentration to 5 mg/ml.) Two new flasks were added at this point, as one uninoculated flask of each medium was dosed with the salt to control for non-biological modifications. These flasks henceforth were treated the same as the inoculated flasks.

Similarly, a sterile 500+ μg/ml dose of compactin was added to three F7 and three K28 flasks of each culture. Two new flasks were added, as one uninoculated flask of each medium was also dosed with compactin. (The purpose of the inoculated compactin flasks was to serve as positive controls, showing that hydroxylation of compactin was occurring normally. The uninoculated flasks served as controls for possible nonbiological alterations of substrate.)

Shaking was resumed for an additional 24 hours. All flasks then received a second dose of the same salt with which they had been dosed previously. Shaking was again resumed for 24 hours, following which eight flasks were harvested (at time $T_1$), including one for each culture-medium-substrate combination. The broths from the harvested flasks were submitted for assay of substrate and hydroxylated product.

Following an additional 24 hours of shaking, the remaining 20 flasks were harvested (at time $T_2$), including 10 methyl compactin salt samples and 10 compactin samples. The broths were submitted for appropriate substrate-product assay.

The results are shown below:

| Culture | Medium | Compactin (μg/g) $T_1$ | $T_2$ | $T_2$ | Pravastatin (μg/g) $T_1$ | $T_2$ | $T_2$ |
|---------|--------|------|------|------|------|------|------|
| A. autotrophica | F7 | 8.4 | 0 | 0 | 474 | 475 | 503 |
|  | K28 | 4.6 | 0 | 0 | 470 | 575 | 512 |
| S. hirsuta | F7 | 842 | 127 | 122 | 347 | 775 | 753 |
|  | K28 | 412 | 0 | 0 | 675 | 750 | 762 |
| None (control) | F7 | — | 1857 | — | — | 0 | — |
|  | K28 | — | 1806 | — | — | 0 | — |

| Culture | Medium | Methyl Compactin (μg/g) $T_1$ | $T_2$ | $T_2$ | Methyl Pravastatin (μg/g) $T_1$ | $T_2$ | $T_2$ |
|---------|--------|------|------|------|------|------|------|
| A. autotrophica | F7 | 0 | 0 | 0 | 57.9 | 56.4 | 55.4 |
|  | K28 | 0 | 0 | 0 | 59.8 | 62.4 | 66.7 |
| S. hirsuta | F7 | 1.7 | 0 | 0 | 71.5 | 77.1 | 82.9 |
|  | K28 | 3.1 | 0 | 0 | 58.9 | 63.3 | 63.8 |
| None (control) | F7 | — | 96.5 | — | — | 0 | — |
|  | K28 | — | 90.2 | — | — | 0 | — |

EXAMPLE 2

One frozen vial of *Saccharapolyspora hirsuta* subspecies *kobensis* (ATCC 20501) was thawed and used to inoculate a 500 ml flask containing 100 ml of medium F4. The flask was placed on a shaker at approximately 280 rpm, at 25° C., and shaken for 72 hours.

Aliquots of the 72 hour broth were used to inoculate two 250 ml flasks containing 45 ml of medium K28. The two flasks were placed on a shaker and shaken at approximately 280 rpm at 25° C.

After 24 hours of shaking, methyl compactin salt was dissolved in water to provide a solution which was filter-sterilized. A portion of this solution was added to one of the K28 flasks. Six hours later, an identical portion was added to the same flask. The second K28 flask also received a portion as did a third uninoculated K28 flask. All three flasks were placed on the shaker and shaking resumed for 18 hours.

The first flask then received a third dose. Six hours later, the first flask received a fourth (and final) dose; the second flask received a second (and final) dose; and the uninoculated flask received a second (and final) dose.

Following an additional 42 hours of shaking, the three flasks were harvested and all of the broths were submitted for assay of methyl compactin and methyl pravastatin. The results are shown below:

| Sample | Methyl Compactin (μg/g) | Methyl pravastatin (μg/g) |
|--------|------|------|
| Flask 1 | 0 | 284.8 |
| Flask 2 | 0 | 251.5 |
| No-cells control | 418.6 | 0 |

EXAMPLE 3

One frozen vial each of *Amycolata autotrophica* (ATCC 35204), *Streptomyces californicus* (ATCC 15436), *Amyco-* lata hydrocarbonoxydans (ATCC 15104), Amycolata mediterranei (ATCC 21411), Amycolatopsis fastidiosa (ATCC 31181) and Saccharopolyspora hirsuta subspecies kobensis (ATCC 20501) were thawed and used to inoculate 500 ml germinator flasks containing 100 ml of medium F7. All flasks were placed on a shaker at approximately 280 rpm, at 25° C., and shaken for 72 hours.

10 ml aliquots from each germinator flask were used to inoculate separate flasks each containing 120 ml of medium K28. All flasks were then returned to the shaker.

After 24 hours, 500 μg/ml of filter sterilized compactin (acid form) was added to each flask. Again the flasks were returned to the shaker.

24 hours later, 15 ml aliquots were removed from each flask and frozen for later assay ($T_1$). A second 500 μg/ml dose of sterile acid-form compactin was added to each flask and the flasks were returned to the shaker.

24 hours after that, a second 15 ml aliquot s ample was removed from each flask and frozen for later assay ($T_2$); and 24 hours after that, a final 15 ml aliquot was removed from each flask and frozen for later assay ($T_3$).

All samples were thawed and submitted for assay. The results are shown in the tables below:

| | $T_1$ | | |
|---|---|---|---|
| Culture | Compactin | Pravastatin | Conversion |
| A. hydrocarbonoxydans | 439 | 0 | — |
| A. mediterranei | 21 | 142 | 28% |
| A. fastidiosa | 376 | 0 | — |
| S. hirsuta | 40 | 201 | 40% |
| Controls: | | | |
| A. autotrophica | 68 | 110 | 22% |
| S. californicus | 0 | 75 | 15% |

| | $T_2$ | | |
|---|---|---|---|
| Culture | Compactin | Pravastatin | Conversion |
| A. hydrocarbonoxydans | 767 | 0 | — |
| A. mediterranei | 15 | 282 | 28% |
| A. fastidiosa | 191 | 0 | — |
| S. hirsuta | 19 | 399 | 40% |
| Controls: | | | |
| A. autotrophica | Trace | 293 | 29% |
| S. californicus | 0 | 167 | 17% |

| | $T_3$ | | |
|---|---|---|---|
| Culture | Compactin | Pravastatin | Conversion |
| A. hydrocarbonoxydans | 812 | 0 | — |
| A. mediterranei | 21 | 290 | 29% |
| A. fastidiosa | 711 | 0 | — |
| S. hirsuta | Trace | 394 | 39% |
| Controls: | | | |
| A. autotrophica | 3 | 276 | 28% |
| S. californicus | 2 | 157 | 16% |

EXAMPLE 4

46-hour cultures of Saccharopolyspora hirsuta subspecies kobensis (ATCC 20501) (grown at 28° C.) and Amycolata autotrophica (ATCC 35204) (grown at 25° C.) were used to inoculate flasks of various media (50 ml media/250 ml flask). 5 ml of innoculum were used per flask.

S. hirsuta was inoculated into two separate flasks of each of the following media: F7, F46, K28, M124, Mueller Hinton, trypticase soy broth (TSB) and Y17. One flask of each medium was placed on a shaker at approximately 280 rpm, at 25° C., and another flask of each medium was placed on a shaker at approximately 280 rpm, at 28° C. An additional flask each of F7 medium and K28 medium was inoculated and placed in a water bath shaker at 32° C.

A. autotrophica was inoculated into two separate flasks each of F7 medium and K28 medium. One inoculated flask of each medium was placed on a shaker at approximately 280 rpm., at 25° C., and one inoculated flask of each medium was placed on a shaker at approximately 280 rpm, at 28° C.

After 24 hours, a 500 μg/g dose of filter sterilized compactin (acid form) was added to each flask. The flasks were returned to the shakers at the same temperature.

24 hours later, a 10 ml aliquot was removed from each flask and frozen for later assay ($T_1$). A second 500 μg/g dose of sterile acid-form compactin was added to each flask and the flasks were again returned to the shakers at the same temperature.

After an additional 48 hours, a second 10 ml aliquot was taken ($T_2$). The $T_1$ samples were thawed and submitted with the T2 samples for assay. The results are shown in the table below:

| S. hirsuta | $T_1$ (frozen and thawed) | | |
|---|---|---|---|
| Medium/Temp. ° C. | Compactin | Pravastatin | Conversion |
| F7/25° | 432 | 40 | 8% |
| F7/28° | 154 | 168 | 34% |
| F7/32° | 450 | 43 | 9% |
| F46/25° | 516 | 10 | 2% |
| F46/28° | 494 | 17 | 3% |
| K28/25° | 179 | 147 | 29% |
| K28/28° | 105 | 184 | 37% |
| K28/32° | 211 | 100 | 20% |
| M124/25° | 180 | 139 | 28% |
| M124/28° | 103 | 191 | 38% |
| Mueller-Hinton/25° | 496 | 38 | 8% |
| Mueller-Hinton/28° | 402 | 43 | 9% |
| TSB/25° | 358 | 74 | 15% |
| TSB/28° | 211 | 163 | 33% |
| Y17/25° | 605 | 0 | — |
| Y17/28° | 533 | 0 | — |
| A. autotrophica (control) F7/25° | 334 | 51 | 10% |
| A. autotrophica (control) F7/28° | 111 | 108 | 22% |
| A. autotrophica (control) K28/25° | 242 | 79 | 16% |
| A. autotrophica (control) K28/28° | 60 | 127 | 25% |

| S. hirsuta | $T_2$ (not frozen) | | |
|---|---|---|---|
| Medium/Temp. ° C. | Compactin | Pravastatin | Conversion |
| F7/25° | 65 | 452 | 45% |
| F7/28° | Trace | 550 | 55% |

-continued

| S. hirsuta | T₂ (not frozen) | | |
|---|---|---|---|
| Medium/Temp. °C. | Compactin | Pravastatin | Conversion |
| F7/32° | Trace | 570 | 57% |
| F46/25° | 965 | 0 | — |
| F46/28° | 999 | 0 | — |
| K28/25° | 0 | 405 | 41% |
| K28/28° | 0 | 405 | 41% |
| K28/32° | 5 | 288 | 29% |
| M124/25° | 233 | 323 | 32% |
| M124/28° | 286 | 303 | 30% |
| Mueller-Hinton/25° | 827 | 121 | 12% |
| Mueller-Hinton/28° | 716 | 81 | 8% |
| TSB/25° | 465 | 238 | 24% |
| TSB/28° | 363 | 289 | 29% |
| Y17/25° | 1086 | 0 | — |
| Y17/28° | 881 | 0 | — |
| A. autotrophica (control) F7/25° | Trace | 266 | 27% |
| A. autotrophica (control) F7/28° | 0 | 220 | 22% |
| A. autotrophica K28/25° | 2 | 266 | 27% |
| A. autotrophica (control) K28/28° | Trace | 257 | 26% |

| S. hirsuta Medium/Temp. °C. | Ratio, T2 Pravastatin: all other products |
|---|---|
| F7/25° | 19.0:1 |
| F7/28° | 13.2:1 |
| F7/32° | 13.3:1 |
| F46/25° | 0.3:1 |
| F46/28° | 0.4:1 |
| K28/25° | 15.7:1 |
| K28/28° | 10.0:1 |
| K28/32° | 10.1:1 |
| M124/25° | 8.4:1 |
| M124/28° | 9.2:1 |
| Mueller-Hinton/25° | 3.9:1 |
| Mueller-Hinton/28° | 4.6:1 |
| TSB/25° | 4.8:1 |
| TSB/28° | 9.6:1 |
| Y17/25° | — |
| Y17/28° | — |
| A. autotrophica F7/25° | 4.2:1 |
| A. autotrophica (control) F7/28° | 5.4:1 |
| A. autotrophica (control) K28/25° | 4.4:1 |
| A. autotrophica (control) K28/28° | 4.5:1 |

EXAMPLE 5

67-hour cultures of various microorganisms grown in F4 medium at 25° C. were used to inoculate 250 ml flasks containing 50 ml of medium F7 and 250 ml flasks containing 50 ml of medium K28. 5 ml of inoculum were used per flask. The organisms used were *Cellulomonas cellulans* (ATCC 12830), *Oerskovia xanthineolytica* (ATCC 27402), *Promicromonospora citrea* (ATCC 15908), *Saccharomonospora viridis* (ATCC 15736), *Saccharopolyspora hirsuta* (ATCC 27875), *Saccharothrix australensis* (ATCC 31497) and *Streptomyces halstedii* (ATCC 13449). *Saccharomonospora viridis* and *S. hirsuta* (ATCC 27875) conversion flasks were placed on a shaker at approximately 280 rpm, at 28° C.; the other cultures were placed on a shaker at approximately 280 rpm, at 25° C. A *Saccharopolysporoa hirsuta* subspecies *kobensis* (ATCC 20501) control was used for both 25° C. and 280C.

After 24 hours, a 500 μg/g dose of compactin was added to each flask.

24 hours later, a second 500 μg/g dose of compactin was added to each flask.

After 96 hours, a 15 ml aliquot was taken from each flask and frozen at −50° C. for later assay.

The samples were thawed and submitted for assay. The results are shown in the table below:

| Culture/ Medium | Temp. | Compactin | Pravastatin | Conversion | Ratio Pravastatin: by-products |
|---|---|---|---|---|---|
| C. cellulans/F7 | 25° C. | 1107 | 0 | — | — |
| C. cellulans/K28 | 25° C. | 1072 | 0 | — | — |
| Oerskovia xanthineolyt./F7 | 25° C. | 1116 | 0 | — | — |
| Oerskovia xanthineolyt./K28 | 25° C. | 688 | 0 | — | — |
| Promicro. citrea/F7 | 25° C. | 1119 | 0 | — | — |
| Promicro. citrea/K28 | 25° C. | 1309 | 0 | — | — |
| Sacchrothrix austral./F7 | 25° C. | 63 | 478 | 43% | 3.1:1 |
| Sacchrothrix austral./K28 | 25° C. | 0 | 465 | 42% | 4.6:1 |
| Streptomyces halsted.F7 | 25° C. | 887 | 0 | — | — |
| Streptomyces halsted./K28 | 25° C. | 1114 | 0 | — | — |
| Saccpolysp. hirsuta ATCC 20501/F7 | 25° C. | 180 | 532 | 48% | 9.4:1 |
| Saccpolysp. hirsuta ATCC 20501/K28 | 25° C. | 73 | 511 | 46% | 9.2:1 |
| F7 blank | 25° C. | 1281 | 0 | — | — |
| K28 blank | 25° C. | 1208 | 0 | — | — |
| Saccharomon. viridis/F7 | 28° C. | 1213 | 0 | — | — |
| Saccharomon. viridis/K28 | 28° C. | 1147 | 0 | — | — |
| Saccharopoly. hirsuta ATCC 27875/F7 | 28° C. | 515 | 92 | 8% | 1.6:1 |
| Saccharopoly. hirsuta ATCC 27875/K28 | 28° C. | 410 | 194 | 18% | 2.0:1 |
| Saccharopoly. hirsuta ATCC 20501/F7 | 28° C. | 35 | 565 | 51% | 12.8:1 |
| Saccharopoly hirsuta ATCC 20501/K28 | 28° C. | 44 | 520 | 47% | 8.7:1 |

EXAMPLE 6

Eight ATCC Mucorales fungi and one *Staurophoma sp.* ATCC 14288 were inoculated from well-grown slants into germinator flasks of medium F4 (100 ml F4/500 ml flasks) and placed on a slow shaker (about 200 rpm) at 25° C. The eight Mucorales fungi were *Absidia ramosa* (ATCC 11613),

*Circinella muscae* (ATCC 16008), *Cunninghamella echinulata* var. *echinulata* (ATCC 36190), *Cunninghamella echninulata* var. *elegans* (ATCC 8688A), *Gilbertella persicaria* (ATCC 38591), *Rhizomucor miehei* (ATCC 26912), *Rhizopus oligosporus* (ATCC 22959) and *Rhizopus stolonifer* (ATCC 14037).

After 72 hours of shaking, the growth in all the germinator flasks looked good except for the *C. echinulata* var. *echinulata* broth which was one large solid fungal mass. This was discarded. The seven remaining Mucorales flasks, and the one Staurophoma flask, were each used to inoculate bioconversion flasks (containing 50 ml medium per 250 ml flasks) of medium F7 and of medium K28. 2 ml of inoculum were used per flask. All flasks were placed on a regular speed (about 280 rpm) shaker at 25° C.

After 24 hours, all flasks received 500 µg/ml dose of compactin, including two uninoculated flasks, one each of media F7 and K28. All flasks were returned to the shaker at 280 rpm and 25° C.

After an additional 24 hours, all flasks received a second 500 µg/ml dose of compactin and were then returned to the shaker.

Forty-eight hours later, samples of 15 to 20 ml were taken from each flask and assayed. The results were as follows:

*Gilbertella persicaria* F7—compactin 621 µg/g; pravastatin 274 µg/g; pravastatin:by-products ratio 2.3:1; and
K28—compactin 822 µg/g; pravastatin 54 µg/g; pravastatin:by-products ratio 3.4:1.

Two of the other cultures showed, at best, trace levels of pravastatin (*Absidia* and *Rhizopus oligosporus*). All the others were negative for pravastatin.

EXAMPLE 7

*Saccharopolyspora hirsuta* subspecies *kobensis* (ATCC 20501) inocula that were two days, three days and four days old in F4 medium (100 ml F4 medium per 500 ml flask, each inoculated with a frozen vial) were used to inoculate bioconversion flasks of medium K28 (50 ml K28 per 250 ml flask). Three flasks of medium K28 were inoculated from each germinator flask, using 5 ml of inoculum. In addition, inoculum from the three day old germinator flask was used to inoculate K28 medium flasks in triplicate with different volumes of inoculum. Specifically, 0.25 ml, 1.0 ml, 2.5 ml, 7.5 ml and 10 ml volumes were used. All flasks were placed on a shaker at approximately 280 rpm, and 28° C.

After 24 hours, a 500 µg/ml dose of compactin sodium salt was added to each flask.

After an additional 24 hours, 1,000 µg/ml compactin sodium salt dose was added to each flask.

Forty-eight hours later, 25 flasks were harvested and sent for assay. The results are as follows:

| Age of Inoculum | Vol. and % Inoculum | Compactin µg/g (Av. of 3) | Pravastatin µg/g (Av. of 3) | Conversion |
|---|---|---|---|---|
| 48 hours | 5 ml (10%) | Trace | 597 | 40% |
| 72 hours | 0.25 ml (0.5%) | 1084 | 138 | 9% |
| 72 hours | 1 ml (2%) | 901 | 211 | 14% |
| 72 hours | 2.5 ml (5%) | 224* | 692 | 46% |
| 72 hours | 5 ml (10%) | Trace** | 676** | 45% |
| 72 hours | 7.5 ml (15%) | 10 | 609 | 41% |
| 72 hours | 10 ml (20%) | Trace | 694 | 46% |
| 96 hours | 5 ml (10%) | Trace | 700 | 47% |
| no inoculum | — | 1201 | 0 | — |

*Result of averaging one flask with 672 µg/g compactin with two flasks showing trace amounts
**Average of two flasks; the possibly contaminated third flask was disregarded \* Result of averaging one flask with 672 µg/g compactin with two flasks showing trace amounts
\*\* Average of two flasks; the possibly contaminated third flask was disregarded

What is claimed is:

1. A method for the preparation of a compound of the formula I:

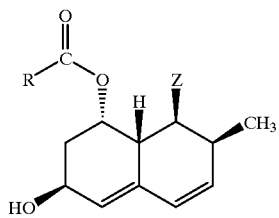

(I)

its partially or completely hydrogenated ring analog or a salt thereof, wherein

R is alkyl or aryl;

Z is the open chain moiety

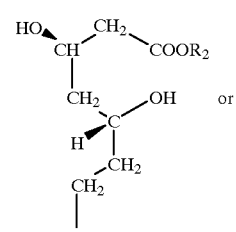

or the lactone

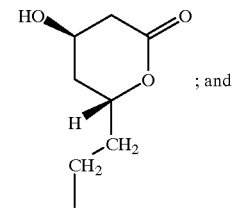

; and $R^2$ is hydrogen, alkyl, ammonium, alkylammonium or alkali metal;

comprising the step of contacting a compound of the formula II:

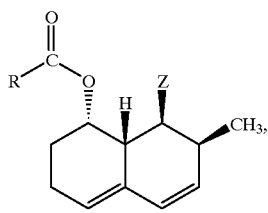
(II)

a partially or completely hydrogenated ring analog or a salt thereof, wherein R, Z and $R^2$ are as defined for formula I, with a microorganism, or with an enzyme derived from, or having the structure of an enzyme derived from, said microorganism, which is capable of catalyzing the hydroxylation of said compound of the formula II or salt thereof to yield said compound of the formula I or salt thereof, and effecting said hydroxylation;

where said microorganism is selected from the genera Nocardia, Amycolata, Saccharopolyspora, Streptomyces, Amycolatopsis, Saccharothrix or Gilbertella, provided that when the compound of formula II is compactin, the microorganism is not Amycolata, Nocardia or Streptomyces.

2. The method of claim 1, wherein Z is said open chain moiety.

3. The method of claim 2, wherein R is alkyl.

4. The method of claim 1, wherein a compound having the following formula:

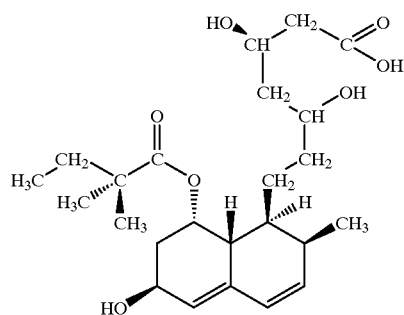

or a partially or completely hydrogenated ring analog, or an alkali metal salt thereof, is prepared.

5. The method of claim 1, wherein the compound of formula II is contacted with a microorganism selected from the genera Nocardia, Amycolata, Saccharopolyspora, Streptomyces, Amycolatopsis, Saccharothrix or Gilbertella, provided that when the compound of formula II is compactin, the microorganism is not Amycolata, Nocardia or Streptomyces.

6. The method of claim 5, wherein said microorganism is *Amycolata autotrophica* ATCC 35204, *Streptomyces californicus* ATCC 15436, *Amycolatopsis mediterranei* ATCC 21411, *Saccharothrix australensis* ATCC 31497, *Gilbertella persicaria* ATCC 38591, *Saccharopolyspora hirsuta* ATCC 27875, *Saccharopolyspora hirsuta* ATCC 27876, *Saccharopolyspora hirsuta* ATCC 20501 or *Saccharopolyspora erythraea* ATCC 11635.

7. The method of claim 6, wherein said microorganism is *Amycolata autotrophica* ATCC 35204 or *Saccharopolyspora hirsuta* ATCC 20501.

8. The method of claim 1, wherein the compound of formula II is dissolved in water or an alcohol before it is contacted with a microorganism or with an enzyme.

9. The method of claim 1, wherein the step of contacting a compound of the formula II with a microorganism or with an enzyme is conducted in an aqueous medium.

10. The method of claim 9, wherein about 0.5 to about 3 mg of a compound of the formula II is contained in each ml of aqueous medium.

11. The method of claim 9, wherein the pH of the aqueous medium is between about 6.0 and about 7.5.

12. The method of claim 9, wherein the temperature of the aqueous medium is between about 27 and 40° C.

13. The method of claim 12, wherein the temperature of the aqueous medium is between about 28 and 34° C.

14. The method of claim 1, wherein the step of contacting a compound of the formula II with a microorganism or with an enzyme continues for between about 2.5 and about 72 hours.

15. The method of claim 1, wherein Z is the lactone.

16. The method of claim 15, wherein the compound of the formula II is hydrolyzed before it is contacted with a microorganism or with an enzyme.

17. The method of claim 1, wherein said compound of the formula I is employed in the preparation of an HMG-CoA reductase inhibitor.

18. A method for the preparation of an HMG-CoA reductase inhibitor, comprising the step of hydroxylating a compound of the formula II, or salt thereof, according to the method of claim 1 to yield a compound of the formula I, or salt thereof.

* * * * *